United States Patent [19]
Afriat et al.

[11] Patent Number: 5,935,559
[45] Date of Patent: *Aug. 10, 1999

[54] SILICONE COMPOSITION CONTAINING A WATER-SENSITIVE ACTIVE AGENT

[75] Inventors: Isabelle Afriat, Paris; Didier Gagnebien, Leclere; Isabelle Pecile, Antony, all of France

[73] Assignee: L'Oreal, Paris, France

[ * ] Notice: This patent is subject to a terminal disclaimer.

[21] Appl. No.: 08/684,908

[22] Filed: Jul. 25, 1996

[30] Foreign Application Priority Data

Jul. 25, 1995 [FR] France ................................... 95-09028

[51] Int. Cl.$^6$ .................................................. A61K 31/69
[52] U.S. Cl. .......................... 424/70.12; 424/59; 524/837; 514/2; 514/167; 514/168; 514/401; 514/458; 514/474; 514/588; 514/781; 514/783; 514/859; 514/938
[58] Field of Search ................................. 524/837; 514/2, 514/167, 168, 401, 458, 474, 588, 781, 783, 859, 938; 424/70.12, 59

[56] References Cited

U.S. PATENT DOCUMENTS

| | | | |
|---|---|---|---|
| 4,341,842 | 7/1982 | Lampe | 428/450 |
| 4,743,474 | 5/1988 | Homan | 427/387 |
| 5,145,907 | 9/1992 | Kalinowski et al. | 524/789 |
| 5,378,455 | 1/1995 | Kealey et al. | 424/73 |
| 5,578,641 | 11/1996 | Jackson et al. | 514/547 |
| 5,624,664 | 4/1997 | Lambrechts | 424/60 |
| 5,703,041 | 12/1997 | Afriat et al. | 514/2 |

FOREIGN PATENT DOCUMENTS

| | | |
|---|---|---|
| 0 330 369 | 8/1989 | European Pat. Off. . |
| 0 516 547 | 12/1992 | European Pat. Off. . |
| 0 611 565 | 8/1994 | European Pat. Off. . |

OTHER PUBLICATIONS

Patent Abstracts of Japan, vol. 7, No. 151 (C–174) [1296], Jul. 2, 1983, & JP–A–58 063750 (Asahi Denka Kogyo K.K.), Apr. 15, 1983.

Chemical Abstracts, vol. 111, No. 6, Aug. 7, 1989, Columbus, Ohio, US; Abstract No. 45032p, p. 367 & JP–A–01 043 342 (Shiseido Co., Ltd) Feb. 15, 1989., Primary Examiner—Margaret W. Glass
Attorney, Agent, or Firm—Oblon, Spivak, McClelland, Maier & Neustadt, P.C.

[57] ABSTRACT

An emulsion comprising an oily phase dispersed in an aqueous phase with the aid of a silicone emulsifying agent, the oily phase comprising at least 50% by weight of silicone oil and the aqueous phase containing at least one polyol in a quantity which imparts a water activity value to the emulsion of ≦0.85.

30 Claims, No Drawings

SILICONE COMPOSITION CONTAINING A WATER-SENSITIVE ACTIVE AGENT

BACKGROUND OF THE INVENTION

1. Field of the Invention

The present invention relates to a stable medium, which is particularly useful in topical applications and which contains an active agent which is sensitive to water. Such compositions are particularly useful in the cosmetic and/or dermatological fields for cleansing and/or caring for and/or protecting the skin and/or keratinous fibers.

2. Description of the Background

It is known to prepare cosmetic and/or dermatological compositions containing active agents which confer specific effects to the skin and/or hair, for example to cleanse the skin, to combat drying, ageing or pigmentation of the skin, to treat acne or some skin diseases (eczema, psoriasis), to combat overweight, to promote the restructuring of the skin or its cellular renewal or to treat seborrhoea of the hair. For example, ascorbic acid (or vitamin C) is known to stimulate the growth of the connective tissue, especially that of collagen. It also strengthens the defense of cutaneous tissue against external aggressive agents such as ultraviolet radiation and pollution. It is also used to remove spots and pigmentation from the skin and also to promote cicatrization of the skin.

It is also known to introduce enzymes into cosmetic compositions, especially proteases for their proteolytic properties. These enzymes are in great demand in the cosmetic field for their smoothing and cleansing power, and for their capacity to remove dead cells from the skin.

Unfortunately, these active agents, as well as others, have the disadvantage of being unstable in aqueous media and of being easily degraded or modified under the influence of water. They thus rapidly lose their activity over time and this instability runs counter to the desired efficacy.

Accordingly, various proposals have been made to overcome these disadvantages. One proposal has been to place an active agent, especially an enzyme, in a pulverulent composition (JP-A-63-130514). Most of the skin cleansing products containing an enzyme exist in this form. It has also been proposed to use these active agents, especially enzymes, in a form in which they are immobilized on polymeric supports (JP-A-61-207499) or in microcapsules (JP-A-61-254244). Unfortunately, some of these techniques require special operations, which increase the cost and the time for preparing the compositions.

Another proposal is the incorporation of the components in an anhydrous liquid medium (U.S. Pat. No. 5,322,683). Unfortunately, this solution limits the galenic form of the composition and does not allow the incorporation of hydrophilic active agents. A need therefore continues to exist for a stable medium which contains hydrophilic and/or lipophilic cosmetic and/or dermatological active agents which are sensitive to water, the active agents retaining all their properties and therefore their efficacy over time.

SUMMARY OF THE INVENTION

Accordingly, one object of the present invention is to provide an oil-in-water emulsion, whose oily phase contains a large quantity of silicone oil, which is capable of maintaining the activity of a water-sensitive active agent and which avoids the degradation of the active agent.

Briefly, this object and other objects of the invention as hereinafter will become more readily apparent can be attained by an emulsion in which an oily phase is dispersed in an aqueous phase with the aid of a silicone emulsifying agent, the oily phase comprising at least 50% by weight of silicone oil, and the aqueous phase containing at least one polyol in an amount which imparts a water activity value to the emulsion of less than or equal to 0.85.

DETAILED DESCRIPTION OF THE PREFERRED EMBODIMENTS

In the cosmetic and/or dermatological fields, a polyol can function as an active agent, especially a moisturizing active agent.

Advantageously, the present emulsion may be used as carrier for a water-sensitive active agent. Thus, another embodiment of the invention is a composition, which contains at least one water-sensitive active agent having topical action and the emulsion as defined above.

Oil-in-water emulsions are known in the cosmetic and dermatological fields whose oily phase contains a high proportion of silicone oil. EP-A-516547 discloses compositions of this type, but it does not teach the introduction of a large quantity of polyol, especially for the purpose of stabilizing the water-sensitive active agents of the composition.

It is also known that the water content of such compositions may influence the stability of water-sensitive active agents. In this regard, D. Tzanos (Behavior of Enzymes By Controlling The Medium Water Activity; Riv. Ital. Essenze, Profumi, Pirante Off., Aromi, Saponi, Cosmet., Aerosol, 1977, vol. 59, No. 5, pages 208–211) proposes the use of surfactants for the stabilization of enzymes onto a porous support. On the other hand, the publication does not lead the skilled artisan to use glycols and does not suggest using a silicone medium.

It has now been found that the degradation of such active agents can be avoided by introducing such agents into the oil-in-water emulsion of the present invention.

In a preferred embodiment of the invention, the quantity of the polyol(s) should be such that the water activity value of the emulsion is less than or equal to 0.7.

The water activity $a_w$ of a water-containing medium is the ratio of the product water vapor pressure "$P_{H2O}$ product" to the vapor pressure of pure water "$P_{H2O}$ pure" at the same temperature. It can also be expressed as the ratio of the number of water molecules "$N_{H2O}$" to the total number of molecules "$N_{H2O}+N_{dissolved\ substances}$", which takes into account the number of molecules of dissolved substances "$N_{dissolved\ substances}$".

It is given by the following formulae:

$$a_w = \frac{P_{H2O}\ \text{product}}{P_{H2O}\ \text{pure}} = \frac{N_{H2O}}{N_{H2O} + N_{dissolved\ substances}}$$

Various methods can be used to measure the water activity. The most common is the manometric method by which the vapor pressure is measured directly.

Conventionally, a cosmetic or dermatologically composition has a water activity in the region of 0.9 to 0.96. Therefore, a water activity of less than 0.85 represents a considerable decrease in water activity.

The polyol employed in the present emulsion is especially glycerin or a glycol such as, in particular, propylene glycol and polyethylene glycols.

According to the invention, the aqueous phase of the emulsion containing the polyol may represent 60 to 90%, preferably 70 to 85% by weight relative to the total weight of the emulsion. In the aqueous phase, the polyol(s) is (are) preferably present in a quantity ranging from at least 30% by weight, preferably from 40 to 90% by weight, and better still from 60 to 85% by weight relative to the total weight of the emulsion.

According to a preferred embodiment of the invention, the polyol(s) exists completely or partly in a complexed form with an acrylic or methacrylic polymer. The polymer may also comprise bound water, that is to say may be complexed with a mixture of water and polyol(s).

Acrylic or methacrylic polymer is understood to be a homopolymer or a copolymer of acrylic or methacrylic acid or a homopolymer or a copolymer of an acrylic or methacrylic acid derivative.

The quantity of such polymers with the complexed polyol (s) and optionally water in the emulsion of the invention ranges from 60 to 90% by weight, preferably from 70 to 85% by weight relative to the total weight of the emulsion.

A suitable homopolymer which complexes water and polyols includes those sold under the tradenames Norgel and Lubrajel CG manufactured by Guardian. These polymers are glyceryl polyacrylates complexed with more than 65% glycerin and/or propylene glycol and less than 35% by weight of bound water. These polymers provide complexes with polyol and water, and are appropriate for the role of gelling agent for the emulsion.

Moreover, the emulsion of the invention may also contain one or several inorganic salts which can diminish the water activity of the emulsion. Suitable such salts include salts of magnesium, calcium and sodium, especially magnesium sulfate, magnesium chloride, calcium chloride and sodium chloride. The quantity of such salt(s) in the emulsion according to the invention ranges from 0.1 to 30% by weight, preferably from 2 to 12% by weight relative to the total weight of the emulsion.

The water-sensitive active agents which may be used according to the invention especially include enzymes such as lactoperoxidase, lipase, protease, phospholipase, cellulases, natural extracts such as green tea, melissa extract, thyme extract, procyannidolic oligomers (PCO) such as hawthorn PCO, pine PCO and grape PCO, vitamins, especially ascorbic acid (vitamin C) and its esters, esters of retinol (vitamin A), phosphated and glucosylated derivatives, urea and rutin.

The preferred water-sensitive active agent(s) is an enzyme, more particularly protease. The protease may be chosen for example from that sold under the tradename "Subtilisine SP 544" manufactured by Novo Nordisk and that sold under the tradename "Lysoveg" manufactured by Laboratoires Sérobiologiques de Nancy.

The quantity of water-sensitive active agent in the emulsion of the invention depends on the type of active agent used. Generally, the active agent(s) may be used in the present emulsion in a quantity ranging from 0.001 to 15% by weight, preferably from 0.01 to 10% by weight relative to the total weight of the emulsion.

The proportion of oily phase in the present emulsion may range from 10 to 40% by weight, and preferably from 15 to 30% by weight relative to the total weight of the emulsion.

The oily phase contains 50 to 100% by weight of organopolysiloxanes, that is to say, silicone oils. These oils represent from 60 to 80% by weight, preferably from 65 to 75% by weight up to the total quantity of oily phase. These silicone oils especially include volatile silicones such as cyclopentadimethylsiloxane and cyclotetradimethylsiloxane, or polydimethylsiloxanes.

The oily phase may comprise, in addition to the silicone oils, hydrocarbon and fluorinated oils. These nonsilicone oils are usually present in a quantity of less than 50% by weight relative to the total weight of the oily phase. Suitable hydrocarbon oils which can be used in the invention, include mineral oils (petroleum jelly), vegetable oils (muscat rose plant oil), animal oils, and synthetic oils. Suitable fluorinated oils include perfluoropolyethers. It is also possible to use fatty substances such as fatty alcohols, fatty acids (stearic acid), waxes and gums (silicone waxes or gums).

The silicone emulsifier used in the present emulsion preferably is a dimethicone copolyol having an HLB (Hydrophilic Lipophilic Balance) value equal to or greater than 10, preferably an alkyldimethicone copolyol chosen from polyoxyethylenated and/or polyoxypropylenated $C_{10}$–$C_{22}$ alkyldimethicone copolyols. Especially preferred is dimethicone copolyol butyl ether sold by Shin-Etsu under the name KF355.

This emulsifier may be present in a proportion ranging from 1 to 10% by weight, preferably from 2 to 5% by weight relative to the total weight of the emulsion.

For topical application, the emulsion of the invention should contain a topically acceptable medium, that is to say a medium which is compatible with the skin and the hair. A composition based on this emulsion, is especially useful for the cleansing, protection, treatment and care of the skin and/or the hair, in particular the face, the neck, the hands, the hair, the scalp and the body, as well as for eyelashes and/or eyebrows.

Thus, an objective of the present invention is to provide a composition for the cleansing and/or protection of skin and/or keratinous fibers, that is to say the hair and/or the eyelashes.

An objective of the present invention is also to provide a cleansing composition for the skin and/or the keratinous fibers in the form of a composition as defined above.

Still another objective of the present invention is a cosmetic and/or dermatological process for cleansing and/or protecting the skin and/or the keratinous fibers by a composition as defined above by applying the composition to the skin and/or the keratinous fibers.

The composition of the invention is especially effective as protective, treating or care creams for the face, for the hands, for the feet or for the hair, as a protective or care body milk or lotion or foam for the care of the skin, the mucous membranes, the hair or the scalp.

The present composition may also contain customary adjuvants in the cosmetic and dermatological fields, such as foaming surfactants, hydrophilic or lipophilic active agents in addition to the water-sensitive active agents, preservatives, antioxidants, solvents, perfumes, fillers, screening agents, odor absorbers and coloring matter. It may also comprise microcapsules, microparticles, or lipid vesicles of the ionic and/or nonionic type. The quantities of these various adjuvants are those conventionally used in the area of use contemplated, and for example are 0.01 to 10% of the total weight of the emulsion. These adjuvants, depending on their nature, may be introduced into the fatty phase, into the aqueous phase and/or into the lipid vesicles.

Suitable hydrophilic active agents include for example, proteins and protein hydrolysates, amino acids, allantoin, sugars and sugar derivatives, and starch.

Suitable lipophilic active agents include for example, tocopherol (vitamin E) and its derivatives, essential fatty acids, ceramides and essential oils.

Having generally described this invention, a further understanding can be obtained by reference to certain specific examples which are provided herein for purposes of illustration only and are not intended to be limiting unless otherwise specified.

EXAMPLE 1

CARE CREAM

| Aqueous phase: | |
| --- | --- |
| Norgel | 82% |
| Dimethicone copolyol butyl ether (KF355 sold by Shin-Etsu) (emulsifier) (HLB = 14.4) | 3% |
| Subtilisine Sp 544 | 0.1% |
| Oily phase: | |
| Muscat rose plant oil | 4.4% |
| Cyclomethicone | 10.5% |

The emulsion is prepared by emulsifying the oily phase in the aqueous phase, with stirring using a homogenizer.

The emulsion obtained has a water activity of 0.64±0.02.

A cream with an iridescent appearance, capable of smoothing the skin and of exfoliating dead cells is obtained.

EXAMPLE 2

CARE CREAM

| Aqueous phase: | |
| --- | --- |
| Norel | 68% |
| Dimethicone copolyol butyl ether (KF355 sold by Shin-Etsu) (emulsifier) (HLB = 14.4) | 3% |
| Subtilisine Sp 544 | 0.1% |
| Oily phase: | |
| Muscat rose plant oil | 8% |
| Cyclomethicone | 20.9% |

The emulsion is prepared in the same manner as described in Example 1. It has a water activity of 0.66±0.02.

A white cream capable of smoothing the skin is obtained.

EXAMPLE 3

CARE CREAM

| Aqueous phase: | |
| --- | --- |
| Glycerin | 30% |
| Propylene glycol | 8% |
| Dimethicone copolyol butyl ether (KF355 sold by Shin-Etsu) (emulsifier) (HLB = 14.4) | 3% |
| Magnesium chloride (anhydrous) | 2% |
| Water | qsp 100% |
| Oily phase: | |
| Muscat rose plant oil | 4.4% |
| Cyclomethicone | 10.5% |

The emulsion is prepared in the same manner as described in Example 1.

A white cream capable of hydrating the skin is obtained.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An emulsion, comprising:
   (A) an oily phase comprising at least 50% by weight of a silicone oil dispersed in (B) an aqueous phase containing at least one polyol in a quantity which imparts a water activity value to the emulsion of $\leq 0.85$, and (C) a silicone emulsifying agent, which emulsifies the two phases (A) and (B), and at least one (D) water-sensitive active agent having topical action.

2. The emulsion according to claim 1, wherein the polyol is present in a quantity such that the water activity value of the emulsion is $\leq 0.7$.

3. The emulsion according to claim 1, wherein the aqueous phase is present in a quantity ranging from 60 to 90% by weight relative to the total weight of the emulsion.

4. The emulsion according to claim 1, wherein the polyol is present in a quantity of at least 30% by weight relative to the total weight of the emulsion.

5. The emulsion according to claim 4, wherein the amount of polyol ranges from 40 to 90% by weight relative to the total weight of the emulsion.

6. The emulsion according to claim 1, wherein the polyol is selected from the group consisting of glycerin and glycols.

7. The emulsion according to claim 1, wherein the polyol is complexed with an acrylic or methacrylic polymer.

8. The emulsion according to claim 7, wherein the polymer further contains bound water.

9. The emulsion according to claim 7, wherein the polymer with the completed polyol and water is present in a quantity ranging from 60 to 90% by weight relative to the total weight of the emulsion.

10. The emulsion according to claim 1, wherein the silicone oil represents 60 to 80% by weight of the oily phase.

11. The emulsion according to claim 1, wherein the silicone oil is selected from the group consisting of volatile silicones and polydimethylsiloxanes.

12. The emulsion according to claim 1, wherein the emulsifying agent has an HLB value $\geq 10$.

13. The emulsion according to claim 1, wherein the emulsifying agent is an alkyldimethicone copolyol.

14. The emulsion according to claim 13, wherein the emulsifying agent is dimethicone copolyol butyl ether.

15. The emulsion according to claim 1, wherein the emulsifying agent is present in a quantity ranging from 1 to 10% by weight relative to the total weight of the emulsion.

16. The emulsion according to claim 1, which further comprises at least one inorganic salt.

17. The emulsion according to claim 16, wherein the inorganic salt is selected from the group consisting of magnesium salts, calcium salts and sodium salts.

18. The emulsion according to claim 16, wherein the salt(s) is present in a quantity ranging from 0.1 to 30% by weight relative to the total weight of the emulsion.

19. The composition according to claim 1, wherein the water-sensitive active agent having topical action is selected from the group consisting of enzymes, natural extracts, procyannidolic oligomers, vitamins, phosphated and glucosylated derivatives, urea and rutin.

20. The composition according to claim 19, wherein said enzyme is protease, said natural extract is green tea and said vitamin is ascorbic acid.

21. The composition according to claim 19, wherein the water-sensitive active agent is present in a concentration ranging from 0.001 to 15% by weight relative to the total weight of the emulsion.

22. The composition according to claim 1, which is a cosmetic and/or dermatological composition.

23. The composition according to claim 1, which further comprises at least one adjuvant selected from the group consisting of preservatives, antioxidants, perfumes, fillers, screening agents, sequestrants, essential oils, coloring matter, hydrophilic active agents, lipophilic active agents and lipid vesicles.

24. A cleansing agent for the skin and/or keratinous fibers, comprising:

(A) at least one water-sensitive active agent having topical action, (B) an emulsion of (i) an oily phase comprising at least 50% by weight of silicone oil dispersed in (ii) an aqueous phase containing at least one polyol in a quantity which imparts a water activity value to the emulsion of $\leq 0.85$, with (c) a silicone emulsifying agent, and (D) at least one adjuvant selected from the group consisting of preservatives, antioxidants, perfumes, fillers, screening agents, sequestrants, essential oils, coloring matter, hydrophilic active agents, lipophilic active agents and lipid vesicles.

25. A method for cleaning and/or protecting the skin or keratinous fibers, which comprises:

applying to said skin and/or keratinous fibers a composition of:

(A) at least one water-sensitive active agent having topical action, (B) an emulsion of (i) an oily phase comprising at least 50% by weight of silicone oil dispersed in (ii) an aqueous phase containing at least one polyol in a quantity which imparts a water activity value to the emulsion of $\leq 0.85$, with (c) a silicone emulsifying agent, and (D) at least one adjuvant selected from the group consisting of preservatives, antioxidants, perfumes, fillers, screening agents, sequestrants, essential oils, coloring matter, hydrophilic active agents, lipophilic active agents and lipid vesicles.

26. An emulsion, comprising:

at least one water-sensitive active agent having topical action; and (A) an oily phase comprising at least 50% by weight of a silicone oil dispersed in (B) an aqueous phase comprising a polyol in a quantity which imparts a water activity value to the emulsion of $\leq 0.85$ complexed with a (meth)acrylic polymer and optionally water of the aqueous phase, and (C) a silicone emulsifying agent, which emulsifies the two phases.

27. The emulsion of claim 26, wherein said (meth)acrylic polymer is a homopolymer or a copolymer of acrylic or methacrylic acid or a homopolymer or copolymer of an acrylic or methacrylic acid derivative.

28. The emulsion of claim 26, wherein the amount of complexed polymer-polyol, optionally with complexed water, in the emulsion ranges from 60–90% by weight.

29. The emulsion of claim 28, wherein said amount of complex ranges from 70–85% by weight of the emulsion.

30. The emulsion of claim 26, wherein the amount of oily phase in the emulsion ranges from 10–40% by weight relative to the total weight of the emulsion.

* * * * *